United States Patent
Mehner et al.

(10) Patent No.: US 6,632,194 B1
(45) Date of Patent: Oct. 14, 2003

(54) DEVICE FOR INSUFFLATING GAS

(75) Inventors: Gotthilf Mehner, Berlin (DE); Eckhard Schramm, Quickborn (DE)

(73) Assignee: W.O.M. World of Medicine GmbH (DE)

( * ) Notice: Subject to any disclaimer, the term of this patent is extended or adjusted under 35 U.S.C. 154(b) by 133 days.

(21) Appl. No.: 09/714,719

(22) Filed: Nov. 16, 2000

(30) Foreign Application Priority Data

Nov. 17, 1999 (DE) .......................................... 199 55 847

(51) Int. Cl.$^7$ ............................................. A61M 37/00
(52) U.S. Cl. ............................... 604/26; 604/23; 604/58
(58) Field of Search ......................... 604/23–26, 82–84, 604/131, 132, 140, 141, 143, 145–147, 58; 128/200.14, 200.21, 200.22, 200.23

(56) References Cited

U.S. PATENT DOCUMENTS

| | | | | |
|---|---|---|---|---|
| 3,640,277 A | * | 2/1972 | Adelberg | 128/DIG. 12 |
| 3,712,298 A | * | 1/1973 | Snowdon et al. | 601/11 |
| 3,880,614 A | * | 4/1975 | Donaldson | 137/360 |
| 3,885,590 A | * | 5/1975 | Ford et al. | 137/505.11 |
| 3,982,533 A | * | 9/1976 | Wiest | 137/557 |
| 4,048,992 A | * | 9/1977 | Lindemann et al. | 604/26 |
| 4,207,887 A | * | 6/1980 | Hiltebrandt et al. | 128/204.23 |
| 4,770,446 A | * | 9/1988 | Keller | 285/141.1 |
| 4,874,362 A | * | 10/1989 | Wiest et al. | 600/560 |
| 4,878,894 A | * | 11/1989 | Sutter et al. | 604/119 |
| 5,006,109 A | * | 4/1991 | Douglas et al. | 600/560 |
| 5,061,268 A | | 10/1991 | Fleenor | |
| 5,098,375 A | | 3/1992 | Baier | |
| 5,122,116 A | * | 6/1992 | Kriesel et al. | 604/122 |
| 5,129,891 A | * | 7/1992 | Young | 285/238 |
| 5,178,612 A | * | 1/1993 | Fenton, Jr. | 285/136.1 |
| 5,246,419 A | * | 9/1993 | Absten | 600/560 |
| 5,267,957 A | * | 12/1993 | Kriesel et al. | 128/DIG. 12 |
| 5,312,337 A | * | 5/1994 | Flaherty et al. | 285/278 |
| 5,354,268 A | | 10/1994 | Peterson et al. | |
| 5,360,396 A | * | 11/1994 | Chan | 600/560 |
| 5,383,874 A | | 1/1995 | Jackson et al. | |
| 5,411,474 A | * | 5/1995 | Ott et al. | 600/560 |
| 5,423,741 A | * | 6/1995 | Frank | 604/23 |
| 5,549,546 A | * | 8/1996 | Schneider et al. | 604/23 |
| 5,620,440 A | * | 4/1997 | Heckele et al. | 392/384 |
| 5,688,256 A | * | 11/1997 | Surratt et al. | 604/19 |
| 5,693,017 A | * | 12/1997 | Spears et al. | 222/22 |
| 5,996,654 A | * | 12/1999 | Green | 141/383 |
| 6,004,509 A | * | 12/1999 | Dey et al. | 134/22.12 |
| 6,068,609 A | * | 5/2000 | Ott et al. | 261/129 |
| 6,158,431 A | * | 12/2000 | Poole | 128/200.16 |
| 6,168,577 B1 | * | 1/2001 | Niederjohn et al. | 604/23 |
| 6,257,626 B1 | * | 7/2001 | Campau | 285/319 |
| 6,299,592 B1 | * | 10/2001 | Zander | 600/560 |
| 6,328,348 B1 | * | 12/2001 | Cornford et al. | 285/305 |
| 6,375,152 B1 | * | 4/2002 | Weh et al. | 251/149.6 |
| 2001/0035649 A1 | * | 11/2001 | Campau | 285/319 |

FOREIGN PATENT DOCUMENTS

| | | |
|---|---|---|
| DE | 39 22 746 | 8/1990 |
| DE | 195 10 710 | 9/1996 |
| DE | 198 22 751 | 9/1999 |
| EP | 0 684 850 B1 | 12/1995 |

* cited by examiner

*Primary Examiner*—Ira S. Lazarus
*Assistant Examiner*—Andrea M. Ragonese
(74) *Attorney, Agent, or Firm*—McGlew and Tuttle, P.C.

(57) ABSTRACT

An insufflation apparatus (2) to be connected through a hose (9) to a gas supply device (3), said hose (9) being connectable to the gas supply device (3) by a hose coupling interface including complementary connection elements (11, 12) at or in gas supply device (3) and at the hose end (9) directed towards the gas supply device, and a sterile filter element (10) being provided. The sterile filter element (10) carries connection element (12) of hose (9).

15 Claims, 3 Drawing Sheets

DEVICE FOR INSUFFLATING GAS

FIELD OF THE INVENTION

The invention relates to a device for insufflating gas into a human or animal body by means of an insufflation apparatus to be connected through a hose to a gas supply device, said hose being connectable to the gas supply device by means of a hose coupling interface comprising complementary connection elements at or in the gas supply device and at the hose end directed towards the gas supply device, and a sterile filter element being provided. —De-vices of the type mentioned above are in particularly used in the fields of endoscopy and laparoscopy. The typically employed gas species is carbon dioxide; however other gases may also be used, for instance with pharmaceutical additions. As an insufflation apparatus can be employed a Veress needle. A gas supply device usually comprises a gas source or a connection to a gas source, a pressure reducer, a flow meter and/or pressure meter, and a control circuitry for controlling pressure or flow, respectively. It is understood that the mentioned components are connected to each other in a suitable way by gas lines (hoses or tubes). The components listed above of a gas supply device are however not the subject matter of the present invention, and for an only exemplary specific embodiment reference is therefore made to document DE 361 101 8 C1.

BACKGROUND OF THE INVENTION

In practical applications, devices of the type mentioned above suffer from the problem of non-sufficient sterility. Basically it is desirable that all components, elements and instruments coming into contact with the gas arc sterile or can be sterilized, respectively, prior to operation. With regard to sterility, however, two fields of problems will have to be taken into account. A first field of problems is that hose connections and tubes within a gas supply device cannot easily be protected from germination. This applies in particular to the process of manufacture, too. Therefore it can be expected that newly supplied gas supply devices internally comprise germs growing in number during continued use. The second field of problems is based on the application of the device. In spite of a gas flow towards the patient, contamination of components of the gas supply device with germs opposite to the gas flow direction cannot be excluded, is under certain conditions even probable. By means of the device, namely, an over-pressure is generated in the body cavity into which gas is introduced. Under special circumstances, for instance by manual pressure on the abdomen, reflux into the gas supply device may occur. Aerosols with body liquid or is body liquid itself may thus enter into the insufflation apparatus, into the hose connected thereto, and into the gas supply device. When using the system on another patient, there is a risk of cross-contamination, even after replacement of the insufflation apparatus and of the hose.

For solving such problems it is well known in the art to arrange a sterile filter between insufflation instrument and gas supply device. The sterile filter is mounted in the hose between gas supply device and insufflation instrument. This is rather awkward and in addition makes the hose unhandy. Further, it cannot be excluded with sufficient reliability for the insofar known device that an operator will not mount a sterile filter at all or will mount a used sterile filter, with the consequence of health risks for the patient.

SUMMARY AND OBJECTS OF THE INVENTION

In contrast thereto, the invention is based on the technical problem to provide a device for insufflating gas, by means of which on one hand sterile working is secured and which on the other hand is easy to handle.

For solving this technical problem the invention teaches that the sterile filter element carries the connection element. In other words, the sterile filter element is not inserted anymore, in an awkward manner, into the hose line, but rather obtains a double function, namely on one hand the arrangement of a sterile barrier and on the other hand as a mechanical connection element for connecting the instrument or the hose thereof to the gas supply device. It is understood that the connection element of the gas supply device is adapted such that a connection cannot be achieved by means of a hose end only. This will lead on one hand to a particularly simple handling. On the other hand, it is achieved as a particularly important advantage that use of the device without a sterile filter element, whether deliberately or inadvertently, is virtually impossible. For a connection of the insufflation instrument or of the hose, respectively, to the gas supply device will only be possible via the sterile filter element. When the sterile filter element is firmly connected with the hose, it is also secured that in case of a rejection of the sterile filter element, also the hose connected thereto is rejected, and vice versa. Moreover, sterile filter element and hose can be packed and kept for later use as a sterile unit. The term firm connection means in this context that the hose cannot be removed by hand from the sterile filter element.

In detail, the construction may be such that the sterile filter element comprises a housing and a filter unit arranged therein, a connection section of the filter housing being adapted as a connection element. When placing and arranging the filter unit, it has to be considered, of course, that the gas will completely flow through the filter unit, and that there are no side ways or leakages for the flowing gas. The filter element may for instance be a membrane filter with a flow capacity of 5–100 liters/min, preferably 16–60 liters/min. As a material may for instance be selected PTFE with a pore size of 1–5 $\mu$m, preferably 3 $\mu$m. Such membrane filters have a filtration efficiency of 99.9998%. In principle, however, all other types of filter elements providing sufficient germ retention and having a sufficiently low gas flow resistance can also be used.

The two complementary connection elements can basically be configured in various ways. For instance, bayonet catches, screw-on or plug-in connections or quick-connect devices being common for hose or line technology are suitable. In a preferred embodiment of the invention, the connection elements comprise complementary dovetail elements that can be slid into each other. With regard to their longitudinal extension, the dovetail elements may be oriented in a surface substantially orthogonal to the gas flow direction; it is also possible to arrange the dovetail elements in a single or double-curved surface (for instance partial cylinder jacket surface or partial spherical surface). In this embodiment, for connecting the hose, the connection element arranged at the sterile filter element is slid into the complementary connection element provided at the gas supply device, and with a complete insertion a lumen of the gas supply device and a lumen of the sterile filter element are opposite to each other (sealed against the environment) and permit gas flow. In this case, one of the connection elements may comprise an actuating element for a shutter provided in the gas supply device, said shutter closing the gas supply device in a gas-tight manner, when the connection element of the hose is not put in place, preferably a gas supply device lumen in the area of the connection element of the gas supply device. The actuating element may be an edge at the sterile filter element pushing the shutter forward when the sterile filter element is slid in, an displaces or swings it from the closed position into the open position. The shutter may be springloaded in the direction of its closed position. In addition, a latch or hold element may be provided in the open position of the shutter, said latch or hold element holding the shutter against the spring force in the open position. This may be achieved in the form of a (mechanically or electrically releasable) latch. Then, in the gas supply device, an actuating element may be provided by means of which this latch is released and—with sufficient spring force on the shutter—throws the sterile filter element by means of the shutter out. It is understood that other control procedures are also possible, for instance by electromotive drives Insofar the actuating element at one of the connection elements may also act in a different way from mechanical. The shutter technology described above in connection with complementary dovetail elements may of course also be adjusted and transferred to other embodiments, which is not difficult using the design knowledge of average man skilled in the art.

A preferred embodiment of the invention of independent inventive importance is characterized by that the sterile filter element comprises a machine-readable ident element, said ident element being provided with the proviso that, when the connection elements are connected to each other, it can be read by means of a reading unit arranged in the gas supply device and connected to an evaluation unit. As ident element is designated a feature containing information about the sterile filter element. Machine-readable ident elements are known in various embodiments and are applicable in the framework of the invention. Examples are: bar code, magnetic tape, micro-chip and hologram. In the case of the magnetic tape and of the microchip, it is also possible to modify and/or complement the information contents of the ident element, then the reading unit having in addition to be adapted in a suitable way as an additional writing unit. In the case of the bar code, the reading unit is an optical scanner. In the case of the magnetic tape, the reading unit is a magnetic reading head, which can simultaneously also be used as a writing head, if necessary. In the case of the micro-chip, the reading unit is a contact field contacting, with connected connection elements, assigned contact fields of the ident element. In the case of the hologram, the reading unit comprises a source of coherent light and a suitable optical sensor circuitry. In any case a suitable conversion of the properties recorded by the reading unit into electrical signals will take place, which, possibly after A/D conversion, are fed as information signals to the preferably digital evaluation unit. The information read-out from the ident element by means of the reading unit is evaluated in the evaluation unit, and according to the result of this evaluation, the gas supply device is cleared or blocked, respectively. For this purpose, the evaluation unit comprises memory elements, wherein the information as well as reference information can be stored or are permanently stored, respectively. In this embodiment, a deliberate or inadvertent re-use of already used sterile filter elements can reliably be prevented by suitable measures in the evaluation unit. For instance, it is possible that an ident element configured as a bar code comprises a code element being different for each sterile filter element (for example coding a serial numbering system). When the sterile filter element is used for the first time, the code element is read and is stored in the evaluation unit as "active". Based on code elements previously stored as "used-up", it is investigated by comparison whether the current individual code element has been read previously already. In case that it is in fact used for the first time, this is not the case, and the gas supply device is cleared. The information of the current code element is then (for instance after throwing the filter element out) stored as "used-up". If however the individual code element has been read previously already, i.e. is stored already as "used-up", the respective sterile filter element is not used for the first time, and the evaluation unit blocks the gas supply device and provides acoustic and/or optical signals. It is also possible that the sterile filter element is automatically thrown out, for instance by operating an electromechanically actuatable latch for the shutter. When for instance a magnetic tape and/or a micro-chip is used, a blocking code can additionally or alternatively written into the ident element, in case of a first use. In case then a re-use of the sterile filter element is attempted, the evaluation unit will identify the blocking code read by means of the reading unit, with the consequence described above of an alarm signal and/or filter element throw-out. In this embodiment it is secured that re-use of a sterile filter element on different units is not possible.

Altogether, by the embodiment of a machine-readable identification or ident element, a very high reliability of the device according to the invention is achieved. It is not a question anymore, what an operator decides about the use of a sterile filter element at all and/or about the re-use of an already used sterile filter element. The device according to the invention will go into proper operation only if a new, i.e. unused sterile filter element has been connected.

In an advantageous improvement of the invention, the ident element comprises a safety element. A safety element is a manually, visually or machine-readable element, which is provided with high protection against falsifying. Safety elements, even machine-readable safety elements, are well known for instance from the technology of banknotes and other means of payment and can be used in corresponding manner in the framework of the present invention. A machine-readable safety element is formed for instance by a hologram. Holograms can be copied with very high technological expenses only, so that application of falsified holograms will be economically unattractive in the framework of the invention. In the case of machine-readable safety elements (in addition to holograms, magnetic safety elements etc. may also be used) an automatic blocking of the gas supply device can be effected by the evaluation unit, for a lacking safety feature and/or non-compliance of the safety element with the requirements, if the reading unit is adapted to read the safety element and/or a safety element reading unit is additionally provided. By such a safety element, a substantially higher degree of safety for patients is achieved, since sterile filter elements of not authorized manufacturers, in particular of cheap products of low quality are not accepted by the evaluation unit. An operator can therefore install only sterile filter elements of quality-supervised authorized manufacturers in order to set the gas supply device into operation. A safety element may also be provided in the ident element as a safety code element.

In another embodiment of the invention, a humidity sensor can be provided in the sterile filter element downstream of filter unit, said humidity sensor being arranged for communication with the evaluation unit, when the connection elements are connected with each other. This embodiment has the following background. Filter elements are or may be hydrophobous and insofar block liquid. These hydrophobous properties are however guaranteed by the manufacturers for a certain period of time only. For safety reasons, it is therefore recommendable to (automatically)

reject a filter unit contacted with liquid. In the embodiment of the invention described here, the humidity sensor preferably arranged close to the filter unit serves for the detection of ingress of liquid or aerosol, respectively. Communication with the evaluation unit can for instance take place via electrical contacts by means of the connection elements. When the humidity sensor indicates that a given limit is exceeded, an alarm signal is generated and/or the gas supply device is stopped. Further, it is possible to mark the sterile filter element as used-up (for instance by blocking the code element in the evaluation unit and/or writing a blocking code into the ident element).

In the framework of the invention, it may be provided that a possible jam of the sterile filter element or of the filter unit due to non-gaseous contaminations occurring in the gas supply and being moved towards the sterile filter element (for instance having the consequence of a disturbing filter cake formation) can automatically be detected and will lead to an alarm signal and/or a throw-out of the sterile filter element, in conjunction with the above measures for preventing a re-use of the sterile filter element. Automatic detection may be performed based on the gas flow being adjustable for certain gas pressures, since the pressure/flow relations are also determined by the flow resistance of the sterile filter element.

The various features of novelty which characterize the invention are pointed out with ell particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENTS

Figure 1:
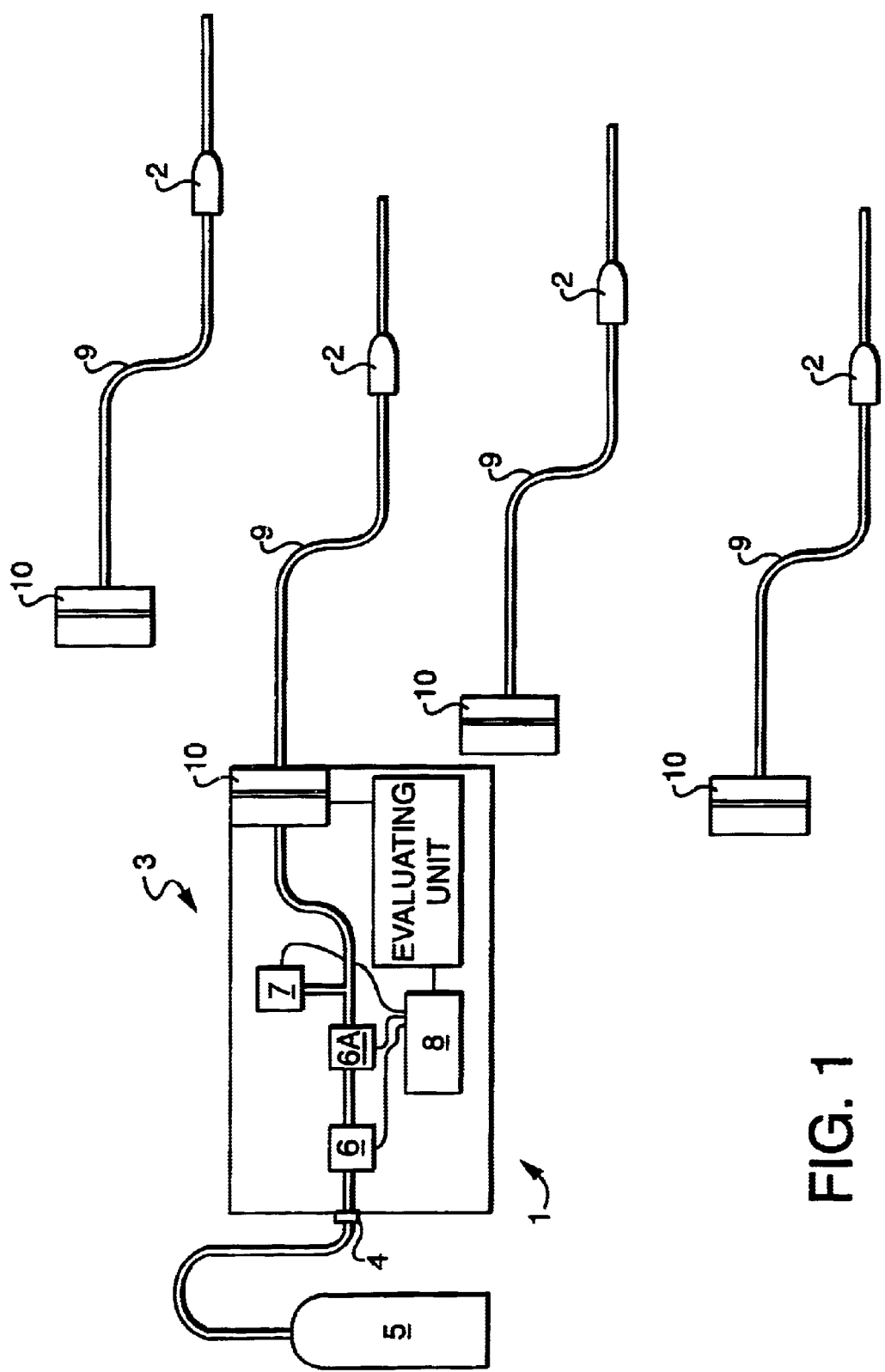
FIG. 1 a total view of a device according to the invention.

In. FIG. 1 can be seen a device for insufflating gas 1 for endoscopy applications. Carbon dioxide is used as gas. The insufflation instrument is a Veress needle 2 to be connected over one of a plurality of hoses 9 with gas supply device 3 by means of a hose coupling interface, said Veress needle being introduced into a human body for the purpose of a medical operation. Gas supply device 3 comprises a port 4 to a carbon dioxide source 5, a pressure reducer 6, a flow meter 6a and pressure meter 7 and a control circuitry 8 for pressure or flow control. It is understood that the mentioned components are connected in suitable way by gas lines (hoses or tubes). In each of the plurality hoses 9 is provided, on the side of the gas supply device, a sterile filter element 10. The hose coupling interface is composed of two complementary connection elements 11, 12, one connection element 11 being formed in the area of the housing of gas supply device 3, and the other connection element 12 being formed by a connection section 13 of a filter housing 14 including a filter unit 15.

Figure 2:
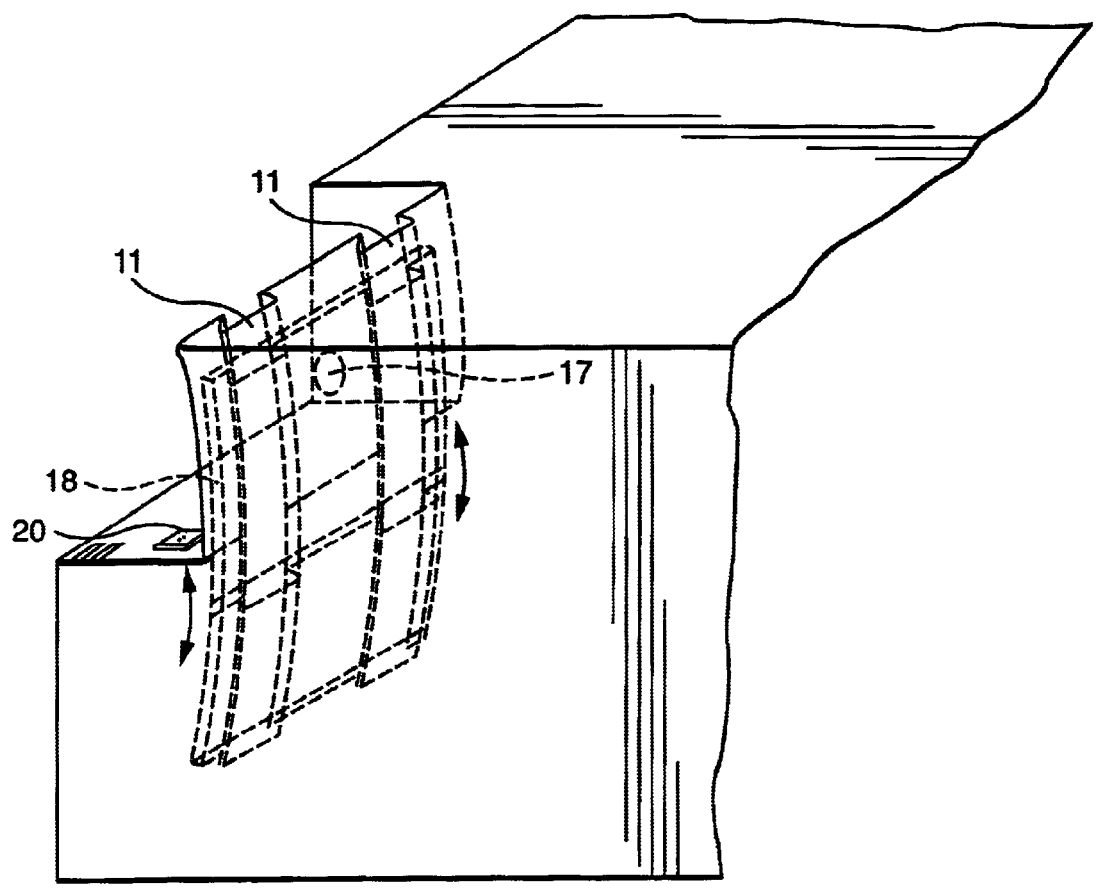
FIG. 2 detail view of the subject matter of FIG. 1 in the area of the connection element on the side of the gas supply device, and FIG. 3 detail view of a sterile filter element applied according to the invention for connection to the subject matter of FIG. 2.
Figure 3:
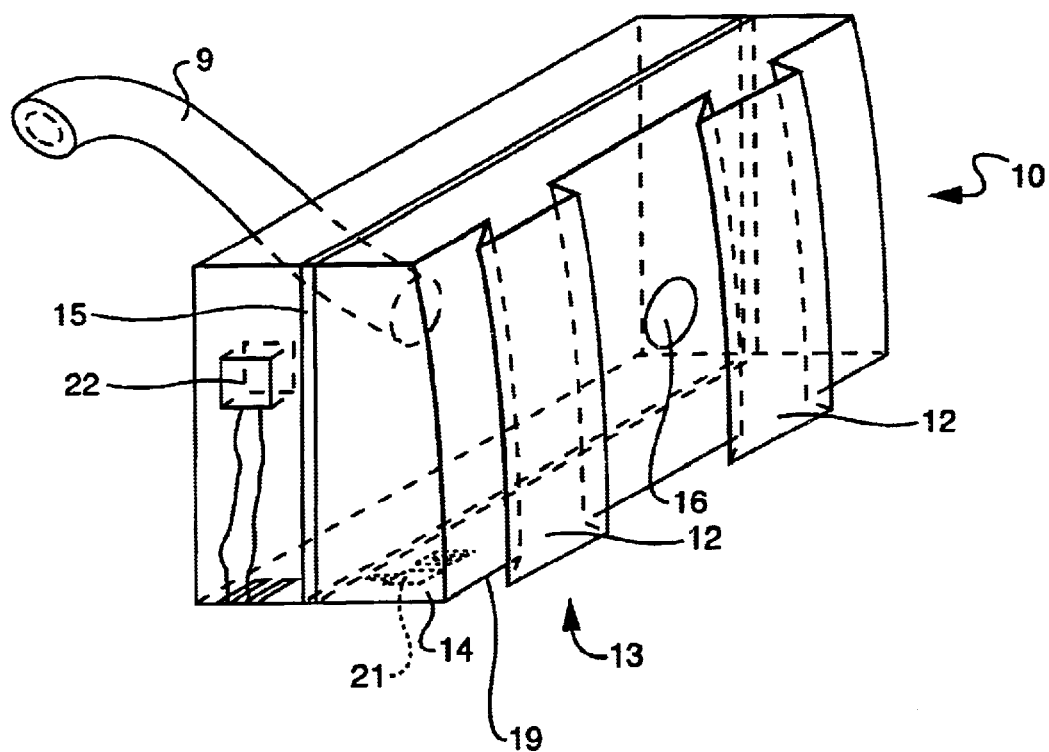

In FIGS. 2 and 3 can be seen that the two connection elements 11, 12 are complementary dovetail elements 11, 12 extending along two parallel partial cylinder jacket surfaces. The two dovetail elements 11, 12 can be slid into each other and thus form a rigid mechanical joint in the pull direction of hose 9. It is understood that dovetail element 11 provided in the area of gas supply device 3 must be accessible from one side, correspondingly for sterile filter element 10. In slid-in condition a sterile filter element lumen 16 and a gas supply device lumen 17 coincide, with the consequence that gas can flow into hose 9. In FIG. 2 can be seen that a shutter 18 is arranged in gas supply device 3, said shutter closing the gas supply device lumen 17 in a gas-tight manner, when sterile filter clement 10 is not slid in. It is not represented that shutter 18 is spring-loaded, in its closed position, and that an electro-mechanically actuatable latch is provided for holding shutter 18 in its open position. When sterile filter element 10 is slid in, shutter 18 is displaced against the spring force from the closed position into the open position. This happens by a stop face 19 of filter housing 14 operating as an actuating element for shutter 18.

In FIG. 3 can be seen that at filter housing 14 is provided a bar code 21, which is individually coded for each sterile filter element 10 and its corresponding one of the plurality of hoses 9. By comparing FIGS. 2 and 3 it can be seen that this bar code 21 comes to rest in slid-in condition of sterile filter element 10 in the area of a reading unit 20 arranged in gas supply device 3, and can be read by said reading unit. Read bar code 21 is compared in an evaluation unit 23 to previously read bar codes which have been stored as "used-up", and only if this comparison has a negative result, control circuitry 8 is activated, with the consequence that a gas flow can only take place in a new sterile filter element 10 with a correspondingly new one of the hoses 9.

Finally, it can be seen in FIG. 3 that a humidity sensor 22 is provided, effecting in case of reflux or aerosols or body liquids an alarm signal and/or a de-activation of gas supply device 3.

What is claimed is:

1. A device for insufflating gas into a human or animal body, the device comprising:
    an insufflation apparatus;
    a gas supply device;
    a hose coupling interface;
    a hose, the insufflation apparatus being connected to said gas supply device via said hose, said hose being connectable to the gas supply device by said hose coupling interface, the hose coupling interface comprising complementary connection elements at or in said gas supply device and at a hose end directed towards the gas supply device;
    a sterile filter element carrying the connection element at said hose end, wherein the sterile filter element is firmly connected to the hose;
    a machine-readable identification element on the sterile filter, said identification element includes a different code element for each sterile filter element, each code element uniquely identifying said each individual filter.

2. A device according to claim 1, wherein said sterile filter element comprises a filter housing and a filter unit arranged therein, said filter housing including a connection section adapted as a connection element.

3. A device according to claim 1, wherein said connection elements comprise complementary dovetail elements adapted to slide into each other.

4. A device according to claim 2, wherein said connection element comprises complementary dovetail elements adapted to slide into each other.

5. A device according to claim 1, wherein at least one of said connection elements comprises an actuating element for a shutter provided in a gas supply device, said shutter closing said gas supply device in a gas-tight manner, when the connection element of said hose end is not put in place.

6. A device according to claim 5, wherein, said shutter closes a gas supply device lumen in the area of connection element of said gas supply device in a gas-tight manner.

7. A device according to claim 1, wherein said identification element is provided with the proviso that, when connection elements are connected to each other, it can be read by means of a reading unit arranged in gas supply device and connected to an evaluation unit.

8. A device according to claim 1, wherein said identification element comprises a safety element.

9. A device according to claim 2, further comprising a humidity sensor; and an evaluation unit, said humidity sensor being provided in said sterile filter element downstream of said filter unit, arranged for communication with the evaluation unit, when said connection elements are connected with each other.

10. A system for insufflating gas into a body, the system comprising:

an insufflation control unit including control circuitry controlling the gas, said insufflation control unit having a first hose coupling;

a plurality of hoses, each hose having one end connectable to the body, and having another end with a second hose coupling, said first and second hose couplings being connectable to each other to pass gas from said insufflation control unit to a respective said hose, said each hose including a sterile filter element;

a machine-readable identification element on said each hose, said identification element includes a different code element for each said hose, each code element uniquely identifying said each individual hose.

11. A system in accordance with claim 10, wherein:

said insufflation control unit includes a reading unit readable of said identification element on said each respective hose when said respective hose is connected to said insufflation control unit;

said insufflation control unit includes an evaluation unit recording said identification elements of connected said hoses, said evaluation unit comparing newly read identification elements with previously read identification elements, said evaluation unit indicating non-operation of said insufflation control unit if said newly read identification element is similar to said previously read identification elements.

12. A system in accordance with claim 10, wherein:

each of said hoses includes a humidity sensor;

said insufflation control unit includes an evaluation unit connectable to said humidity sensor of a connected said hose, said evaluation unit indicating non-operation of said insufflation control unit if said humidity sensor indicates fluids from the body in said respective hose.

13. A system in accordance with claim 10, wherein:

said filter includes a filter housing formed as part of said second hose coupling;

said first hose coupling being shaped to be not directly connectable to a hose.

14. A device in accordance with claim 7, wherein:

said evaluation unit compares newly read identification elements with previously read identification elements, said evaluation unit indicating non-operation of said insufflation apparatus if said newly read identification element is similar to said previously read identification elements.

15. A device in accordance with claim 9, wherein:

said evaluation unit indicates non-operation of said insufflation control unit if said humidity sensor indicates fluids from the body in said hose.

* * * * *